(12) United States Patent
Chou et al.

(10) Patent No.: US 8,016,988 B2
(45) Date of Patent: Sep. 13, 2011

(54) GAS SENSOR

(75) Inventors: Chen-Chia Chou, Taipei (TW);
Tsung-Her Yeh, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 369 days.

(21) Appl. No.: 12/168,338

(22) Filed: Jul. 7, 2008

(65) Prior Publication Data

US 2009/0013761 A1    Jan. 15, 2009

(30) Foreign Application Priority Data

Jul. 10, 2007  (TW) ................................ 96125048 A

(51) Int. Cl.
*G01N 27/407* (2006.01)
*G01N 27/26* (2006.01)
(52) U.S. Cl. .................. 204/424; 204/426; 73/31.05
(58) Field of Classification Search ............ 73/31.05; 204/424, 425, 426, 427
See application file for complete search history.

(56) References Cited

U.S. PATENT DOCUMENTS

| 4,980,044 | A | * | 12/1990 | Ker ......................... 204/426 |
| 5,419,828 | A | * | 5/1995 | Nakano et al. ............. 204/425 |
| 5,830,339 | A | * | 11/1998 | Watanabe et al. ........... 204/426 |
| 6,797,138 | B1 | * | 9/2004 | Detwiler et al. ............ 204/427 |
| 2005/0252770 | A1 | * | 11/2005 | Naito et al. ............... 204/424 |
| 2007/0012566 | A1 | * | 1/2007 | Nair et al. ................. 204/431 |
| 2007/0023296 | A1 | * | 2/2007 | Cai et al. .................. 205/782 |

* cited by examiner

*Primary Examiner* — Lisa M Caputo
*Assistant Examiner* — Punam Roy

(57) ABSTRACT

A gas sensor is provided. The gas sensor includes a post, an ion conductive layer, a first sensing portion and a second sensing portion. The post includes a first end, a second end, a side surface and a groove, wherein the groove is formed on the side surface of the post, and an opening is formed on the first end connecting with the groove. The ion conductive layer is formed on the side surface of the post, including a first surface and a second surface, wherein the first surface is opposite to the second surface, and the ion conductive layer and the groove compose a chamber. The first sensing portion is formed on the first surface. The second sensing portion is formed on the second surface corresponding to the first sensing portion, wherein the first sensing portion is located in the chamber.

18 Claims, 4 Drawing Sheets

GAS SENSOR

CROSS REFERENCE TO RELATED APPLICATIONS

This Application claims priority of Taiwan Patent Application No. 096125048, filed on Jul. 10, 2007, the entirety of which is incorporated by reference herein.

BACKGROUND OF THE INVENTION

1. Field of the Invention

The present invention relates to a gas sensor, and in particular relates to an oxygen sensor.

2. Description of the Related Art

FIG. 1 shows a conventional oxygen sensor 10 comprising a first electrode 11, a second electrode 12, a chamber 13, an ion conductive layer 14 and a gas selective layer 15. The chamber 13 is formed in a center of the ion conductive layer 14. A first electrode 11 is formed on an inner wall of the chamber 13. The second electrode 12 is formed on an outer wall of the ion conductive layer 14. The gas selective layer 15 is coated on the second electrode 12. In gas detection, the chamber 13 is connected to an environmental gas, the environment gas reacts with the first electrode 11, and a gas to be measured passes the gas selective layer 15 to react with the second electrode 12. The oxygen consistency of the environmental gas differs from that of the gas to be measured. Thus, a voltage difference is formed between the first electrode 11 and the second electrode 12. The voltage difference generates an electromotive force to conduct the first electrode 11 and the second electrode 12 through the ion conductive layer 14. The oxygen consistency of the gas to be measured is obtained by measuring the voltage difference.

Conventionally, the ion conductive layer 14 is made by an injection, a dry press or an extrusion process. A conventional ion conductive layer 14 is thick with minimal sensitivity and high costs.

BRIEF SUMMARY OF THE INVENTION

A detailed description is given in the following embodiments with reference to the accompanying drawings.

A gas sensor is provided. The gas sensor comprises a post, an ion conductive layer, a first sensing portion and a second sensing portion. The post comprises a first end, a second end, a side surface and a groove, wherein the groove is formed on the side surface of the post, and an opening is formed on the first end connecting with the groove. The ion conductive layer is formed on the side surface of the post, comprising a first surface and a second surface, wherein the first surface is opposite to the second surface, and the ion conductive layer and the groove compose a chamber. The first sensing portion is formed on the first surface. The second sensing portion is formed on the second surface corresponding to the first sensing portion, wherein the first sensing portion is located in the chamber.

The invention supports the ion conductive layer (or combined material with cermet or metal) with a post or body to increase structural strength. The ion conductive layer thus can be formed by a thick film process or a thin film process. Thus, the thickness of the ion conductive layer is reduced, and sensitivity thereof is increased. The gas sensor of the invention has increased operating lifespan and reduced cost when compared with conventional gas sensors.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
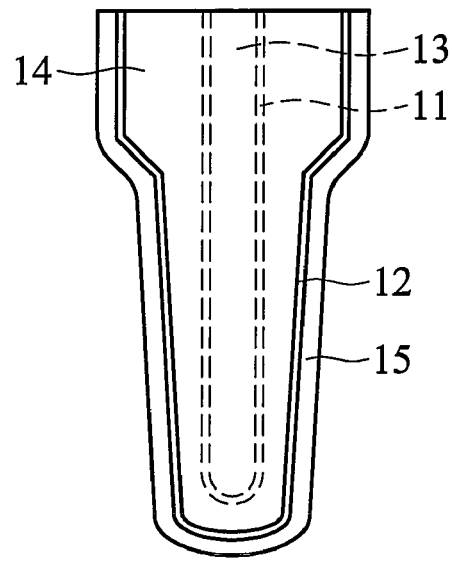
FIG. 1 shows a conventional oxygen sensor.
Figure 2:
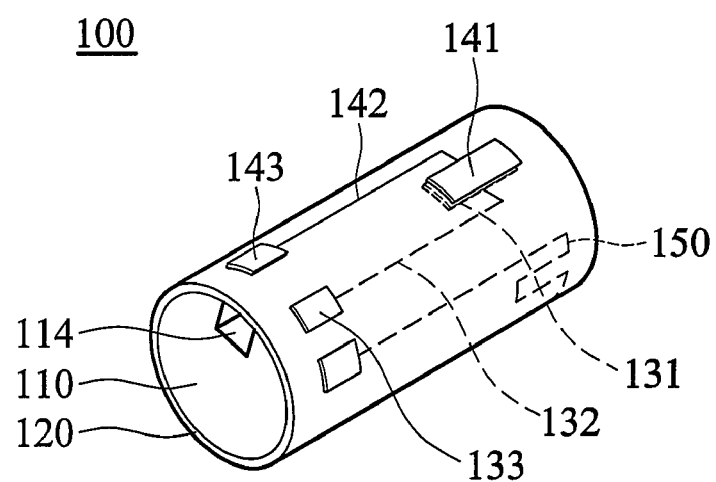
FIG. 2 shows a gas sensor of a first embodiment of the invention.

FIG. 2 shows a gas sensor 100 of a first embodiment of the invention, comprising a post 110, an ion conductive layer 120, a first sensing portion 131, a second sensing portion 141 and a heating element 150. The post 110 comprises a groove 114. The groove 114 is formed on a side surface of the post 110. The ion conductive layer 120 is formed on the side surface of the post 110. The ion conductive layer 120 comprises a first surface and a second surface. The second surface is opposite to the first surface. The ion conductive layer 120 and the groove 114 compose a chamber. The first sensing portion 131 is formed on the first surface. The second sensing portion 141 is formed on the second surface. The second sensing portion 141 is corresponding to the first sensing portion 131. The first sensing portion 131 is located in the chamber.

During gas detection, the chamber (composed of by the groove 114 and the ion conductive layer 120) is connected to an environmental gas. The environment gas reacts with the first sensing portion 131. A gas to be measured contacts the second sensing portion 141, and reacts with the second sensing portion 141. The oxygen consistency of the environmental gas differs from that of the gas to be measured. Thus, a voltage difference is formed between the first sensing portion 131 and the second sensing portion 141. The voltage difference generates an electromotive force. The oxygen consistency of the gas to be measured is obtained by measuring the voltage difference.

In the first embodiment of the invention, the post 110 supports the ion conductive layer 120. The ion conductive layer thus can be formed on the post 110 by a thick film or a thin film process. Thus, the thickness of the ion conductive layer is reduced, and sensitivity thereof is increased. The gas sensor of the first embodiment of the invention has increased operating lifespan and reduced cost when compared with conventional gas sensors.

Figure 3A:
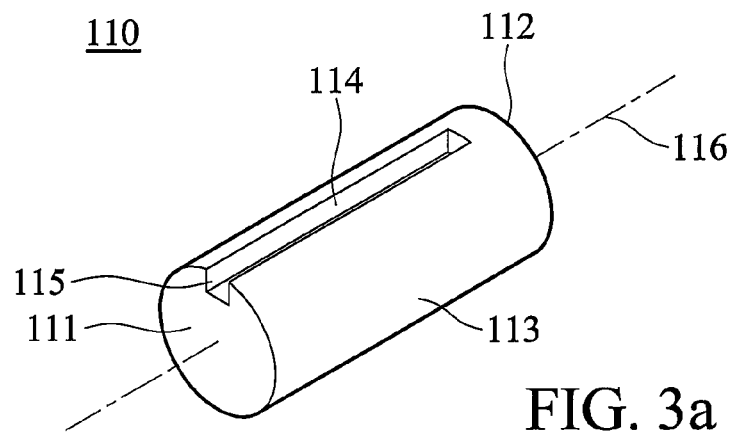
FIG. 3a shows a detailed structure of the post.
Figure 3B:
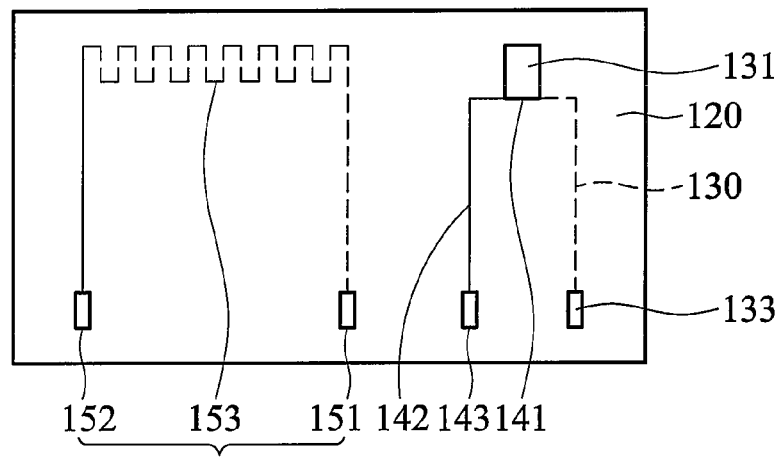
FIG. 3b is a top view of the ion conductive layer.
Figure 3C:
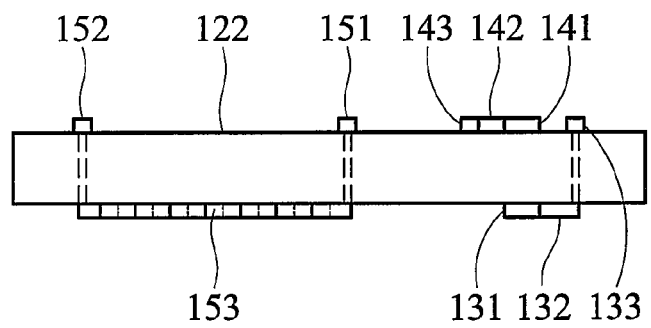
FIG. 3c is a side view of the ion conductive layer.

FIGS. 3a to 3c show a detailed structure of the gas sensor 100. With reference to FIG. 3a, the post 110 is a cylinder, comprising a first end 111, a second end 112, a side surface 113 and a groove 114. The groove 114 is formed on the side surface 113. An opening 115 is formed on the first end 111, and connected to the groove 114. The groove 114 extends parallel to a major axis 116 of the post 110. In the embodiment, the groove 114 does not contact the second end 112. A minimum cross-section area of the groove is 1 mm².

The post 110 is made of a structural ceramic or an electronic ceramic, such as a zirconium oxide base (3Y-TZP+ YNbO$_4$ system 18 Mpa/m$^{1/2}$), a zirconium oxide base with aluminum oxide (hominess phase), a cerium oxide base with aluminum oxide (hominess phase), a Perovskite (ABO$_3$) with aluminum oxide (hominess phase) or a tungsten carbide cermet with zirconium oxide to provide tenacity. The post 110 can be formed by a slip casting, a press molding, an (heat) injection printing or an injection process. The post of the embodiment has a simple structure, and can be mass produced to decrease costs.

With reference to FIGS. 3b and 3c, the conductive layer 120 comprises a first surface 121 and a second surface 122. The second surface 122 is opposite to the first surface 111. The first sensing portion 131 is formed on the first surface 121. The second sensing portion 141 is formed on the second surface 122 corresponding to the first sensing portion 131. The heating element 150 comprises a first contact 151, a second contact 152 and a heating wire 153. The first contact 151 and the second contact 152 are formed on the second surface 122. The heating wire 153 is disposed in the ion conductive layer 120 or in the post 110, or disposed on the surface of the ion conductive layer 120 or the post 110.

The gas sensor 100 further comprises a first connection portion 133, a first conductive portion 132, a second connection portion 143 and a second conductive portion 142. The first conductive portion 132 is electrically connected to the first sensing portion 131 and the first connection portion 133. The second conductive portion 142 is electrically connected to the second sensing portion 141 and the second connection portion 143. With reference to FIG. 2, the first connection portion 133 and the second connection portion 143 are separately corresponding to two sides of the groove. The first conductive portion 132 is connected to the first connection portion 133 on the second surface 122 via the through hole.

The ion conductive layer can comprise cerium oxide or zirconium oxide mixed with positive ion with +2 or +3 charges. The ion-conductive material, proton-conductive material or electron-conductive material can also be LaMo$_2$O$_9$, Perovskite or Ga—Mg—Sr—La. The ion conductive layer 120 can be formed by a thick film process, such as a screen print, a dry press, an injection printing, a scrape, a spreading or an immersion plating process. The ion conductive layer 120 also can be formed by a thin film process of Micro Electro-Mechanical Systems, such as lift-off process.

The first sensing portion comprises a first catalyzer layer, and the second sensing portion comprises a second catalyzer layer. The first and second catalyzer layers can comprise the following materials: (a) metal materials such as Pt, Au, Pd, Rh, Ir, Ru, Os, Ni, Co and Fe which can easily electrical-chemical react with oxygen; (b) Perovskite ceramics such as LaSrMnO$_3$ and LaSrCoFeO$_3$, which can easily electrical-chemical react with oxygen; (c) a combined material comprising the metal materials and the Perovskite ceramics mentioned above with zirconium oxide to provide ion-conduction and electron-conduction; and (d) a second phase material for resisting carbonization, poisoning or vulcanization, such as copper or cerium oxide. The first and second catalyzer layers can be formed by a thick film process, such as a screen print, an injection print, a spread or an immersion plating process. The first and second catalyzer layers can also be formed by a thin film process, such as a lift-off process.

Figure 4:
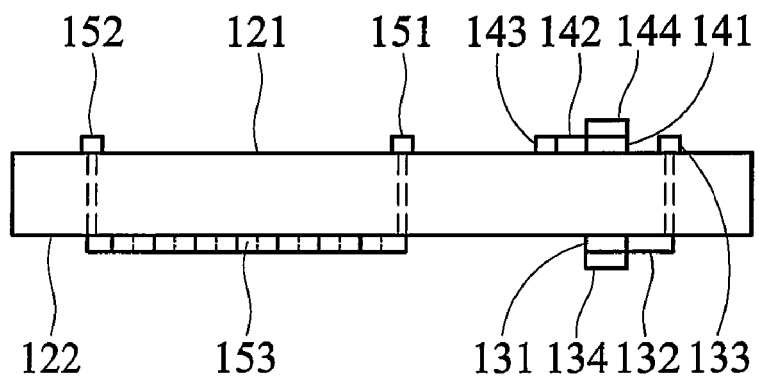
FIG. 4 shows the first embodiment comprising a gas diffusion layer.

With reference to FIG. 4, in a modified embodiment of the invention, a first gas diffusion layer 134 is formed on a surface of the first sensing portion 131, and a second gas diffusion layer 144 is formed on a surface of the second sensing portion 141. The first and second gas diffusion layers can comprise (a) hexagonal prism porous material, such as LaAl$_{11}$O$_8$ or LaAlO$_3$, or (b) magnesium aluminate spinel. The first and second gas diffusion layers can be formed by a thick film process, such as A screen print, A dry press, a scrape, an injection print, a spread or an immersion plating process. The first and second catalyzer layers can also be formed by a thin film process, such as a lift-off process.

Figure 5:
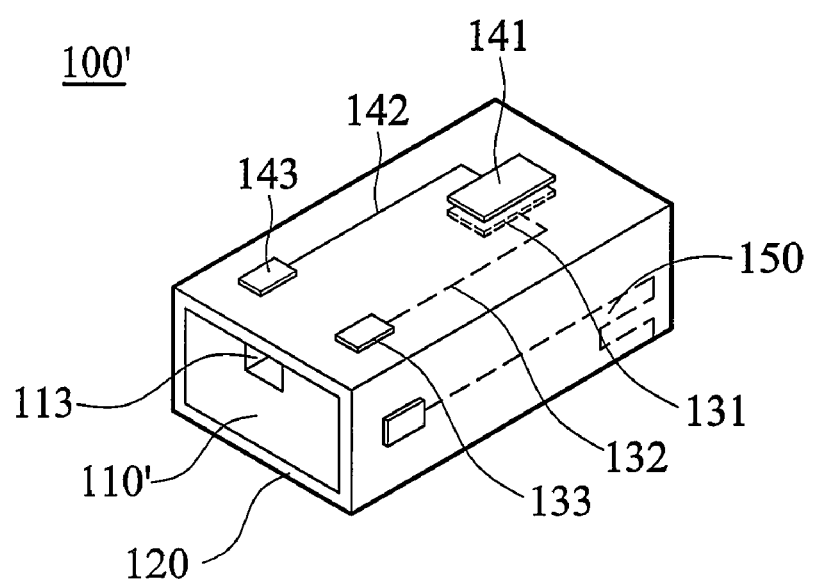
FIG. 5 shows a gas sensor of a modified embodiment of the first embodiment of the invention.

FIG. 5 shows a gas sensor 100' of a modified embodiment of the first embodiment of the invention, wherein the post 110' is rectangular. In the invention, the shape of the post can be modified. Note that the embodiments do not limit the invention.

Figure 6:
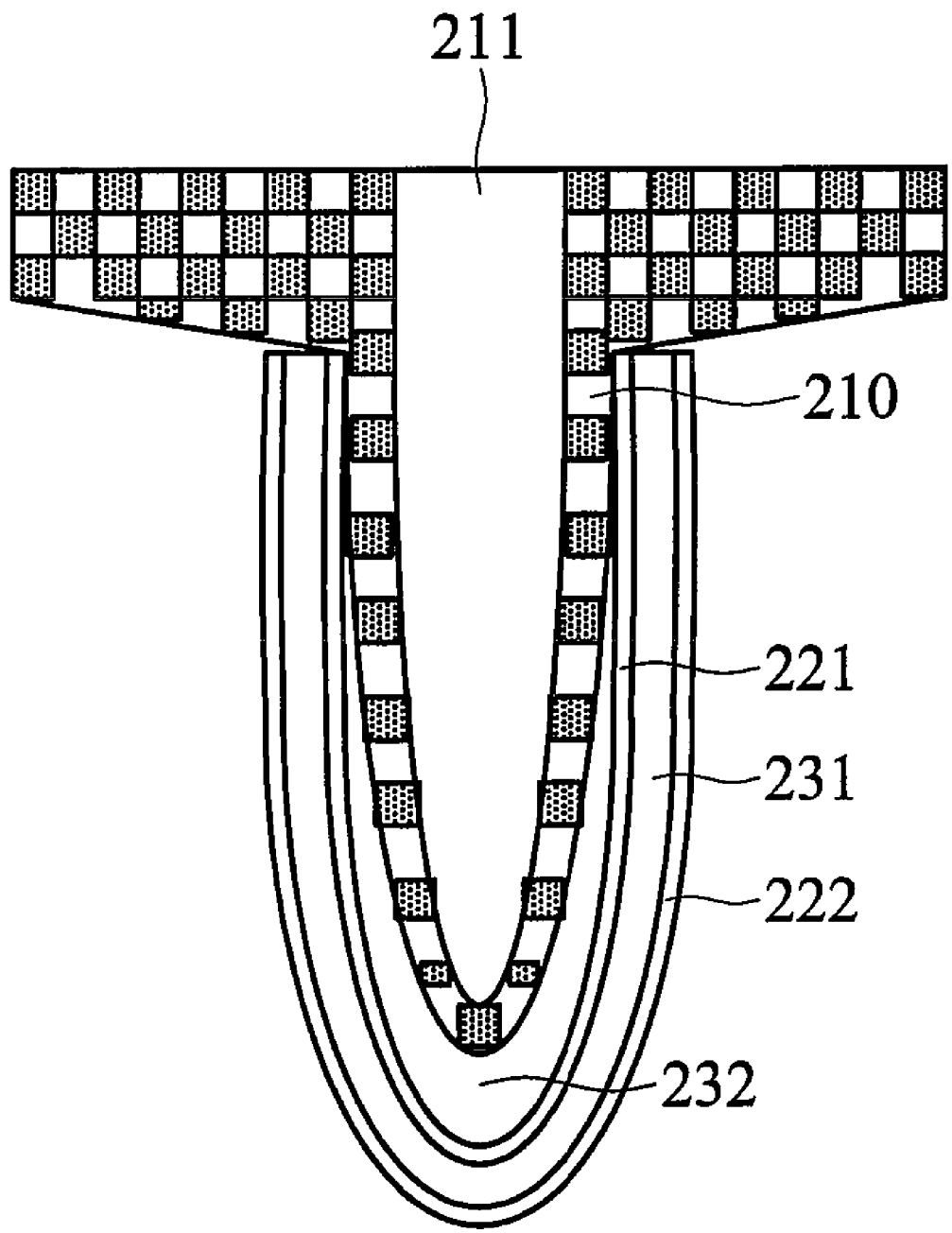
FIG. 6 shows a gas sensor of a second embodiment of the invention.

FIG. 6 shows a gas sensor 200 of a second embodiment of the invention, comprising a body 210, a first electrode layer 221, a second electrode layer 222, a first ion conductive layer 231 and a second ion conductive layer 232. The body 210 comprises a chamber 211. The body 210 is formed by a porous material. The second ion conductive layer 232 is coated on an outer surface of the body 210. The first electrode 221 is coated on an outer surface of the second ion conductive layer 232. The first ion conductive layer 231 is coated on an outer surface of the first electrode layer 221. The second electrode layer 222 is coated on an outer surface of the first ion conductive layer 231. The first ion conductive layer 231 is sandwiched between the first electrode layer 221 and the second electrode layer 222.

During detection, the chamber 211 is connected to an environmental gas, the environmental gas passes the body 210 and the second ion conductive layer 232 to react with the first electrode layer 221, and a gas to be measured contacts the second electrode layer 222 to react therewith. The oxygen consistency of the environmental gas differs from that of the gas to be measured. Thus, a voltage difference is formed between the first electrode layer 221 and the second electrode layer 222. The voltage difference generates an electromotive force. The oxygen consistency of the gas to be measured is obtained by measuring the voltage difference.

Similar to the first embodiment, the body 210 of the second embodiment supports the first ion conductive layer 231. The first ion conductive layer 231 thus can be formed on the body 210 by a thick film or a thin film process. The thickness of the first ion conductive layer 231 is reduced, and sensitivity of the gas sensor is increased.

The body 210 can be formed by a conductive porous metal or a conductive porous ceramic, such as a porous stainless steel, a porous Perovskite conductive ceramic with hominess phase material (tungsten carbide cermet with a zirconium oxide combined ceramic), a Perovskite comprising a conductive ceramic (LaSrMnO$_3$, LaSrCoO$_3$, LaSrCoFeO$_3$) or a combined material having porous metal and conductive ceramic. In a modified embodiment, the body 210 is made of a conductive porous metal to provide a heating function, such that an additional heating element is not required.

When the body 210 is made of non-conductive porous metal, the second ion conductive layer 232 can be omitted.

The first ion conductive layer 231 and the second ion conductive layer 232 are formed by a heat spreading, an immersion plating or a spin coating process. The first ion conductive layer 231 and the second ion conductive layer 232 comprise materials selected from a group of zirconium oxide, cerium oxide, LaMo$_2$O$_9$, Perovskite and Ga—Mg—Sr—La.

Similar to the first embodiment, the first and second electrode layers can comprise: (a) metal materials such as Pt, Au, Pd, Rh, Ir, Ru, Os, Ni, Co and Fe which can easily electrical-chemical react with oxygen; (b) Perovskite ceramics such as LaSrMnO$_3$ and LaSrCoFeO$_3$, which can easily electrical-chemical react with oxygen; (c) a combined material comprising the metal materials and the Perovskite ceramics mentioned above with zirconium oxide to provide ion-conduction and electron-conduction; and (d) a second phase material for resisting carbonization, poisoning or vulcanization, such as copper or cerium oxide. The first and second electrode layers can be formed by a thick film process, such as a screen print, an injection print or a spread process. The first and second catalyzer layers can also be formed by a thin film process, such as a lift-off.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A gas sensor, comprising
   a post, comprising a first end, a second end, a side surface and a groove, wherein the groove is formed on the side surface of the post, and an opening is formed on the first end connecting with the groove;
   an ion conductive layer, formed on the side surface of the post, comprising a first surface and a second surface, wherein the first surface is opposite to the second surface, and the ion conductive layer and the groove compose a chamber;
   a first sensing portion, formed on the first surface;
   a second sensing portion, formed on the second surface in a position corresponding to the first sensing portion, wherein the first sensing portion is located in the chamber;
   a first connection portion;
   a first conductive portion; and
   a second connection portion and a second conductive portion;
   wherein the first conductive portion is electrically connected to the first sensing portion and the first connection portion, and the second conductive portion is electrically connected to the second sensing portion and the second connection portion; and
   wherein the first sensing portion comprises a first gas diffusion layer, and the second sensing portion comprises a second gas diffusion layer.

2. The gas sensor as claimed in claim 1, wherein the post is cylinder.

3. The gas sensor as claimed in claim 1, wherein the post is rectangular.

4. The gas sensor as claimed in claim 1, wherein the groove extends parallel to a major axis of the post.

5. The gas sensor as claimed in claim 1, wherein the first connection portion and the second connection portion are separately corresponding to two sides of the groove.

6. The gas sensor as claimed in claim 1, wherein the first sensing portion comprises a first catalyzer layer, and the second sensing portion comprises a second catalyzer layer.

7. The gas sensor as claimed in claim 1, wherein the ion conductive layer comprises materials selected from a group of zirconium oxide, cerium oxide, LaMo2O9, Perovskite and Ga—Mg—Sr—La.

8. The gas sensor as claimed in claim 1, further comprising a heating wire, disposed in the ion conductive layer.

9. The gas sensor as claimed in claim 1, wherein the post comprises materials selected from a group of zirconium oxide base, zirconium oxide base with aluminum oxide, cerium oxide base with aluminum oxide, Perovskite with aluminum oxide and tungsten carbide cermet with zirconium oxide.

10. A gas sensor, comprising
    a post, comprising a first end, a second end, a side surface and a groove, wherein the groove is formed on the side surface of the post, and an opening is formed on the first end connecting with the groove;
    an ion conductive layer, formed on the side surface of the post, comprising a first surface and a second surface, wherein the first surface is opposite to the second surface, and the ion conductive layer and the groove compose a chamber;
    a first sensing portion, formed on the first surface;
    a second sensing portion, formed on the second surface in a position corresponding to the first sensing portion, wherein the first sensing portion is located in the chamber; and
    a heating wire, disposed in the ion conductive layer.

11. The gas sensor as claimed in claim 10, wherein the post is cylinder.

12. The gas sensor as claimed in claim 10, wherein the post is rectangular.

13. The gas sensor as claimed in claim 10, wherein the groove extends parallel to a major axis of the post.

14. The gas sensor as claimed in claim 10, further comprising a first connection portion, a first conductive portion, a second connection portion and a second conductive portion, wherein the first conductive portion is electrically connected to the first sensing portion and the first connection portion, and the second conductive portion is electrically connected to the second sensing portion and the second connection portion.

15. The gas sensor as claimed in claim 14, wherein the first connection portion and the second connection portion are separately corresponding to two sides of the groove.

16. The gas sensor as claimed in claim 14, wherein the first sensing portion comprises a first catalyzer layer, and the second sensing portion comprises a second catalyzer layer.

17. The gas sensor as claimed in claim 10, wherein the ion conductive layer comprises materials selected from a group of zirconium oxide, cerium oxide, LaMo2O9, Perovskite and Ga—Mg—Sr—La.

18. The gas sensor as claimed in claim 10, wherein the post comprises materials selected from a group of zirconium oxide base, zirconium oxide base with aluminum oxide, cerium oxide base with aluminum oxide, Perovskite with aluminum oxide and tungsten carbide cermet with zirconium oxide.

* * * * *